United States Patent

Siegel et al.

[11] Patent Number: 5,710,341
[45] Date of Patent: Jan. 20, 1998

[54] PREPARATION OF α-CHLOROALKYL ARYL KETONES

[75] Inventors: Wolfgang Siegel, Limburgerhof; Walter Dobler, Heidelberg; Michael John, Lambsheim, all of Germany

[73] Assignee: BASF Aktiengesellschaft, Ludwigshafen, Germany

[21] Appl. No.: 620,317

[22] Filed: Mar. 22, 1996

[30] Foreign Application Priority Data

Mar. 31, 1995 [DE] Germany .......... 195 11 861.8

[51] Int. Cl.⁶ .................................................. C07C 45/63
[52] U.S. Cl. ................................. 568/316; 568/312
[58] Field of Search ................................. 568/316

[56] References Cited

U.S. PATENT DOCUMENTS 4,310,702  1/1982  Masilamani et al. .............. 568/348

OTHER PUBLICATIONS

J.achem Soc 1989 III, 6796–6799.
Database WPI, Section Ch, Week 8626, Class E14, AN 86–165167 (English abstract of JP-A 61 097 239, May 15, 1986.
Database WPI, Section Ch, Week 9348, Class B05, An 93–383022 (English abstract of JP-A 05 286 902, Nov. 2, 1993.

Olivato et al., *Magn. Reson. Chem.* (MRCHEG, 07491581), 1987, vol. 25 (2), pp. 179–180.
Lands et al., J. Med. Chem. 35 (1992) 3081–3084.

*Primary Examiner*—Alan L. Rotman
*Assistant Examiner*—Jean F. Vollano
*Attorney, Agent, or Firm*—Keil & Weinkauf

[57] ABSTRACT

A process for preparing α-chloroalkyl aryl ketones of the formula I

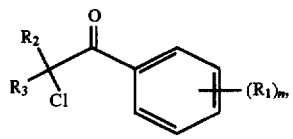

where
n is 1 to 5,
$R_1$ independently of one another are H, alkyl, alkoxy, aryl, aryloxy, acyloxy, acylamino, halogen or nitro,
$R_{2,3}$ independently of one another are H, alkyl or aryl, by chlorination of alkyl aryl ketones of the formula II

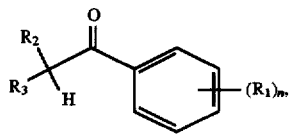

with sulfuryl chloride is described, the chlorination being carried out in the presence of an aliphatic alcohol.

4 Claims, No Drawings

PREPARATION OF α-CHLOROALKYL ARYL KETONES

BACKGROUND OF THE INVENTION

1. Field of the Invention

The present invention relates to a novel process for preparing α-chloroalkyl aryl ketones.

α-Chloroalkyl aryl ketones are useful intermediates for the synthesis of pharmaceutical and crop protection active compounds. They were previously prepared, inter alia, by reacting alkyl aryl ketones with a chlorinating reagent.

2. Description of the Related Art

Lands et al. (J. Med. Chem. 35 (1992), 3081–3084) describe the following reaction:

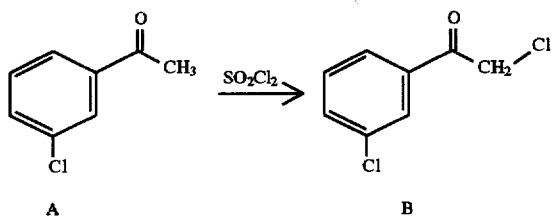

A     B which yields the product B in 41% yield. Our own experiments with $SO_2Cl_2$ as the chlorinating reagent show that, depending on the reaction procedure, either unsatisfactory yields or excessively low selectivities are achieved in the chlorination.

It is an object of the present invention to make available a process for preparing α-chloroalkyl aryl ketones by chlorination of alkyl aryl ketones with $SO_2Cl_2$ in which the abovementioned disadvantages do not occur.

SUMMARY OF THE INVENTION

We have found that improved results are achieved by a process for preparing α-chloroalkyl aryl ketones of the formula I

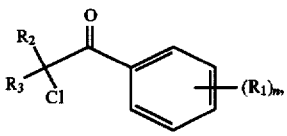   I where n is 1 to 5, $R_1$ independently of one another are H, alkyl, alkoxy, aryl, aryloxy, acyloxy, acylamino, halogen or nitro, $R_{2,3}$ independently of one another are H, alkyl or aryl, by chlorination of alkyl aryl ketones of the formula II

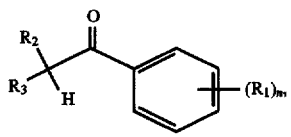   II with sulfuryl chloride, the chlorination being carried out in the presence of an aliphatic alcohol.

DESCRIPTION OF PREFERRED EMBODIMENTS

Saturated or unsaturated aliphatic alcohols are suitable for the process according to the invention. Saturated unbranched or branched-chain alcohols are preferably used, in particular those having 1 to 10 C atoms.

Particularly preferred alcohols are methanol, ethanol, 1-propanol, 2-propanol, 1-butanol and 2-butanol.

The alcohols can be employed in the process according to the invention either as individual substances or as mixtures.

Good results can be achieved if the aliphatic alcohols are employed in amounts from 0.1 mol to 10 mol, preferably from 2 mol to 6 mol, per mole of alkyl aryl ketone. Lower molar ratios than those indicated as a rule lead to significant side reactions, while higher molar ratios mostly lead to incomplete conversion.

As a rule, sulfuryl chloride is employed in an amount from 1 mol to 2 mol, preferably 1.0 mol to 1.5 mol, per mole of alkyl aryl ketone II.

Amounts of $SO_2Cl_2$ outside these particulars can be employed, but lead to no improvement in the process according to the invention.

Since α-chloroalkyl aryl ketones of the formula I as a rule are solids, the reaction is preferably carried out in a solvent. Suitable solvents are all those which readily dissolve both the alkyl aryl ketones II employed and the resulting α-chloroalkyl aryl ketones I and do not enter into any reaction with sulfuryl chloride under the reaction conditions. Aromatic hydrocarbons such as benzene, toluene, ethylbenzene, xylenes such as o-xylene and tetralin; haloaromatics such as chlorobenzene and dichlorobenzenes, eg. 1,2-dichlorobenzene, saturated aliphatic hydrocarbons of the empirical formula $C_nH_{2n+2}$ where n=from 5 to 20 such as hexane, heptane and octane, and chlorinated aliphatic hydrocarbons, eg. methylene chloride, chloroform, tetrachloromethane, 1,1-dichloroethane, 1,2-dichloroethane, 1,1,1-trichloroethane and 1,1,2-trichloroethane and mixtures of these are particularly suitable.

The reaction is preferably carried out at normal pressure, since an increase or decrease in the pressure is not accompanied by any significant advantages with respect to selectivity, yield and process technology.

The reaction can be carried out in a temperature range from −80° C. to +100° C., preferably in the range 0° C. to 50° C. Reaction temperatures outside this range give no significant advantages with respect to selectivity, yield and process technology, but lead to unnecessarily high costs because of the rising energy requirement for cooling or heating.

The reaction can be carried out either batchwise or continuously in suitable apparatuses.

The alkyl aryl ketones of the formula II employed in the process according to the invention are known, commercially available or can be prepared, for example, from aromatic hydrocarbons and carbonyl halides according to Friedel-Crafts (Houben Weyl, "Methoden der organischen Chemie" (Methods of Organic Chemistry), Georg Thieme Verlag, Stuttgart 1973, Volume 7/2a, part 1, pages 23 to 107 and pages 135–154).

The following examples serve to illustrate the invention in greater detail and demonstrate the prior art (comparison examples).

EXAMPLE 1

General working procedure

The amounts indicated in Table 1 of the alkyl aryl ketones 1a to 1d and alcohols 2a to 2c indicated in scheme 1 and also the amounts of sulfuryl chloride, methylene chloride and water indicated in Table 1 were used. The reaction temperatures indicated in Table 1 were established.

The alkyl aryl ketones 1a to 1d were initially introduced in a mixture of methylene chloride and one of the aliphatic alcohols 2a to 2c into a stirring apparatus having a thermostated double jacket. The desired reaction temperature has been established by heating or cooling the apparatus with the aid of a thermostat. A solution of sulfuryl chloride in methylene chloride was metered into the stirred reaction mixture in the course of 1 hour while maintaining the reaction temperature with the aid of an automatic metering device. The mixture was subsequently stirred at constant temperature for one hour and water was then added to the reaction mixture. Conversion and selectivity of the chlorinating reaction were determined by gas-chromatographic analysis of the organic phase.

addition of an aliphatic alcohol. The numbering relates to scheme 1.

Scheme 1

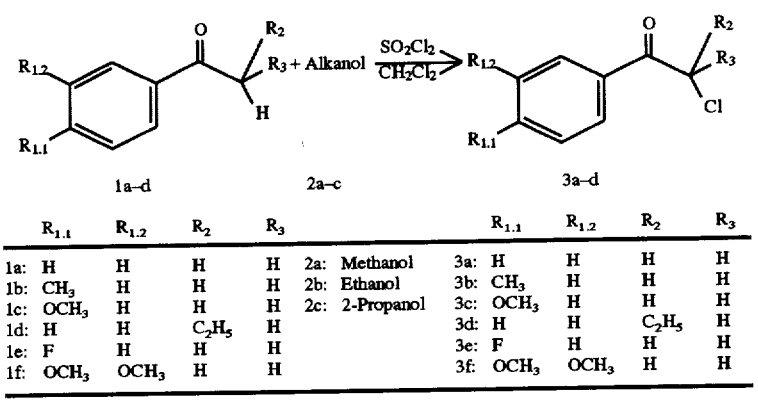

|    | $R_{1.1}$ | $R_{1.2}$ | $R_2$    | $R_3$ |     |              |     | $R_{1.1}$ | $R_{1.2}$ | $R_2$    | $R_3$ |
|----|-----------|-----------|----------|-------|-----|--------------|-----|-----------|-----------|----------|-------|
| 1a:| H         | H         | H        | H     | 2a: | Methanol     | 3a: | H         | H         | H        | H     |
| 1b:| $CH_3$    | H         | H        | H     | 2b: | Ethanol      | 3b: | $CH_3$    | H         | H        | H     |
| 1c:| $OCH_3$   | H         | H        | H     | 2c: | 2-Propanol   | 3c: | $OCH_3$   | H         | H        | H     |
| 1d:| H         | H         | $C_2H_5$ | H     |     |              | 3d: | H         | H         | $C_2H_5$ | H     |
| 1e:| F         | H         | H        | H     |     |              | 3e: | F         | H         | H        | H     |
| 1f:| $OCH_3$   | $OCH_3$   | H        | H     |     |              | 3f: | $OCH_3$   | $OCH_3$   | H        | H     |

TABLE 1

| Alkyl aryl ketone [mmol] | Methylene chloride [ml] | Alcohol [mmol] | Sulfuryl chloride [mmol] | Methylene chloride [ml] | Water [ml] | Temperature [20 C.] | Conversion[1] [%] | Selectivity[2] [%] |
|---|---|---|---|---|---|---|---|---|
| 1a-100 | 50 | 2a-400 | 140 | 20 | 50 | 20 | 96.5 | >99 |
| 1b-100 | 50 | 2a-400 | 140 | 20 | 50 | 20 | 95.8 | >99 |
| 1c-100 | 50 | 2a-400 | 140 | 20 | 50 | 20 | 97.3 | 98.9 |
| 1d-100 | 50 | 2a-400 | 140 | 20 | 50 | 20 | >99 | 97.5 |
| 1e-100 | 50 | 2a-400 | 140 | 20 | 50 | 20 | 97.8 | 97.3 |
| 1f-100 | 50 | 2a-400 | 140 | 20 | 50 | 20 | 97.6 | 97.1 |
| 1c-100 | 50 | 2b-400 | 140 | 20 | 50 | 20 | 87.8 | 96.7 |
| 1c-100 | 50 | 2c-400 | 140 | 20 | 50 | 20 | 75.1 | 93.4 |
| 1c-100 | 50 | 2a-400 | 140 | 20 | 50 | 10 | >99 | 94.7 |
| 1c-100 | 50 | 2a-400 | 140 | 20 | 50 | 40 | 98.6 | 95.6 |
| 1c-100 | 50 | 2a-400 | 100 | 20 | 50 | 20 | 67.0 | >99 |
| 1c-100 | 50 | 2a-400 | 160 | 20 | 50 | 20 | >99 | 87.6 |
| 1c-100 | 50 | 2a-200 | 140 | 20 | 50 | 20 | >99 | 78.4 |
| 1c-100 | 50 | 2a-600 | 140 | 20 | 50 | 20 | 91.3 | 98.5 |

[1] based on alkyl aryl ketones 1
[2] based on α-chloroalkyl aryl ketones 3

EXAMPLE 2

(Comparison example, not according to the invention)

The comparison experiment from Table 2 was carried out by the general working procedure of Example 1, but without

TABLE 2

| Alkyl aryl | Methylene | | Sulfuryl | Methylene |

| ketone [mmol] | chloride [ml] | Alcohol [mmol] | chloride [mmol] | chloride [ml] | Water [ml] | Temperature [20 C.] | Conversion[1] [%] | Selectivity[2] [%] |
|---|---|---|---|---|---|---|---|---|
| 1a-100 | 50 | — | 140 | 20 | 50 | 20 | >99 | 76.2 |
| 1b-100 | 50 | — | 140 | 20 | 50 | 20 | >99 | 57.0 |
| 1c-100 | 50 | — | 140 | 20 | 50 | 20 | >99 | 64.3 |

[1] based on alkyl aryl ketones 1
[2] based on α-chloroalkyl aryl ketones 3

We claim:

1. A process for preparing α-chloroalkyl aryl ketones of the formula I

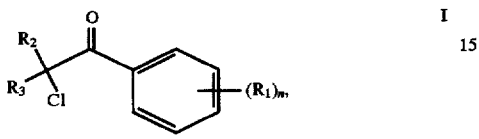

where n is 1 to 5, $R_1$ independently of one another are H, alkyl, alkoxy, aryl, aryloxy, acyloxy, acylamino, halogen or nitro, $R_{2,3}$ independently of one another are H, alkyl or aryl, by chlorination of alkyl aryl ketones of the formula II

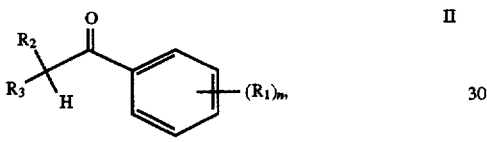

with sulfuryl chloride, which comprises carrying out the chlorination in the presence of an aliphatic alcohol.

2. The process of claim 1, wherein from 0.1 to 10 mol of alcohol are employed per mole of alkyl aryl ketone II.

3. The process of claim 1, wherein a $C_1$–$C_4$-alcohol is employed.

4. The process of claim 3, wherein the alcohol employed is methanol.

* * * * *